US00PP14592P29

(12) United States Plant Patent
Noodelijk

(10) Patent No.: US PP14,592 P2
(45) Date of Patent: Mar. 9, 2004

(54) CHRYSANTHEMUM PLANT NAMED 'AMOR DARK PINK'

(50) Latin Name: *Chrysanthemum morifolium*
Varietal Denomination: Amor Dark Pink

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 59 days.

(21) Appl. No.: 10/317,050

(22) Filed: Dec. 12, 2002

(51) Int. Cl.[7] ..... A01H 5/00
(52) U.S. Cl. ..... Plt./287
(58) Field of Search ..... Plt./287

*Primary Examiner*—Anne Marie Grunberg
(74) *Attorney, Agent, or Firm*—Parkhurst & Wendel, L.L.P.

(57) ABSTRACT

A chrysanthemum plant named 'Amor Dark Pink' characterized by its medium sized blooms with pink ray florets and prolific branching; natural season flower date September 4–9; blooming for a period of 7 weeks.

3 Drawing Sheets

Related cultivars: 'Amor Dark Pink' is related to 'Amor' (U.S. Plant Pat. No. 13,046). 'Amor Dark Pink' is a color mutant of 'Amor'.

BACKGROUND OF THE INVENTION

'Amor Dark Pink' is a product of a breeding and selection program which had the objective of finding color mutants of 'Amor'. The new plant of the present invention comprises a new and distinct cultivar of chrysanthemum plant that is a natural occuring sport of a parent chrysanthemum named 'Amor' (U.S. Plant Pat. No. 13,046). A comparison with Parent chrysanthemum 'Amor' is also made in this application. The new cultivar was discovered as a sport in September 1999 by Rob Noodelijk in a controlled environment (greenhouse) in Rijsenhout Holland. The first act of asexual reproduction of 'Amor Dark Pink' was accomplished when vegetative cuttings were taken from the initial selection in October 1999 in Rijsenhout Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
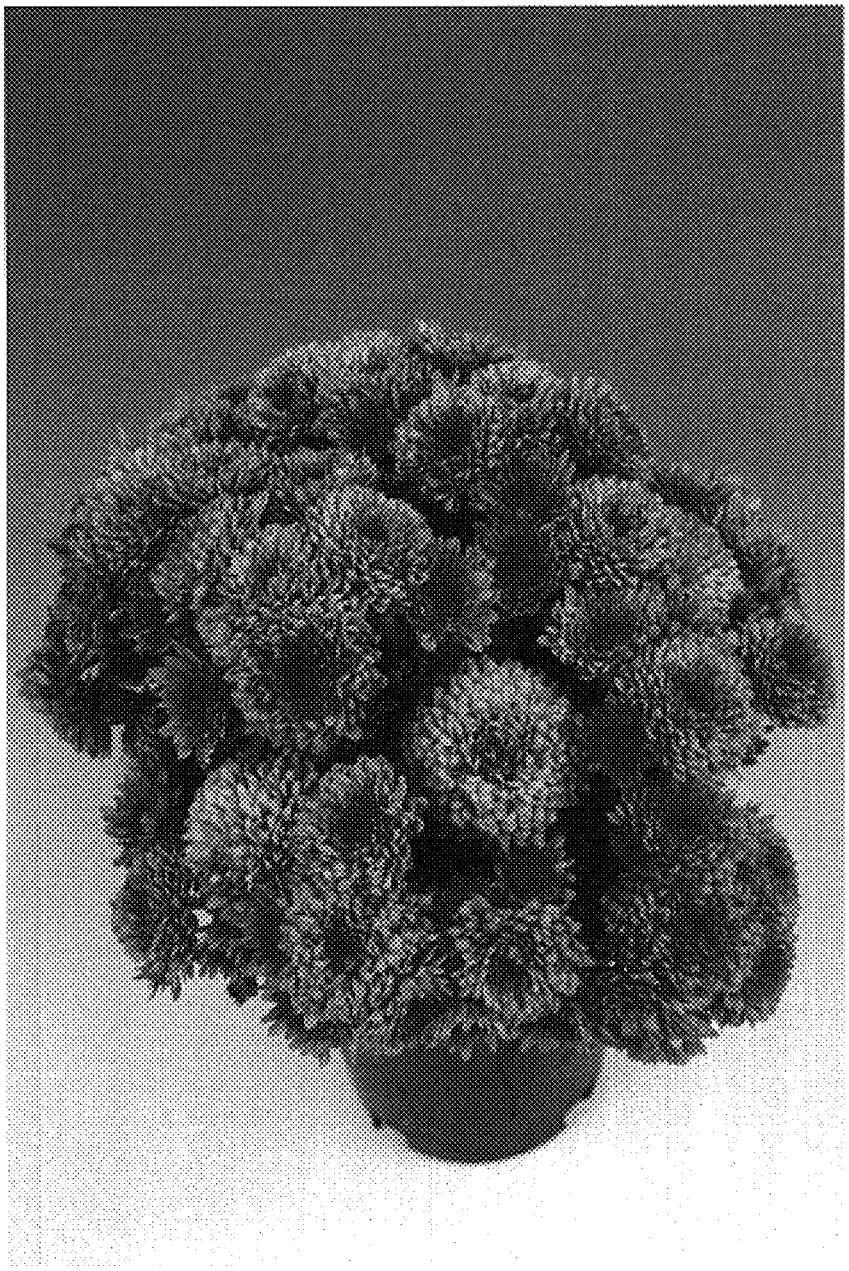
FIG. 1 shows a plant of the cultivar in full bloom.
Figure 2:
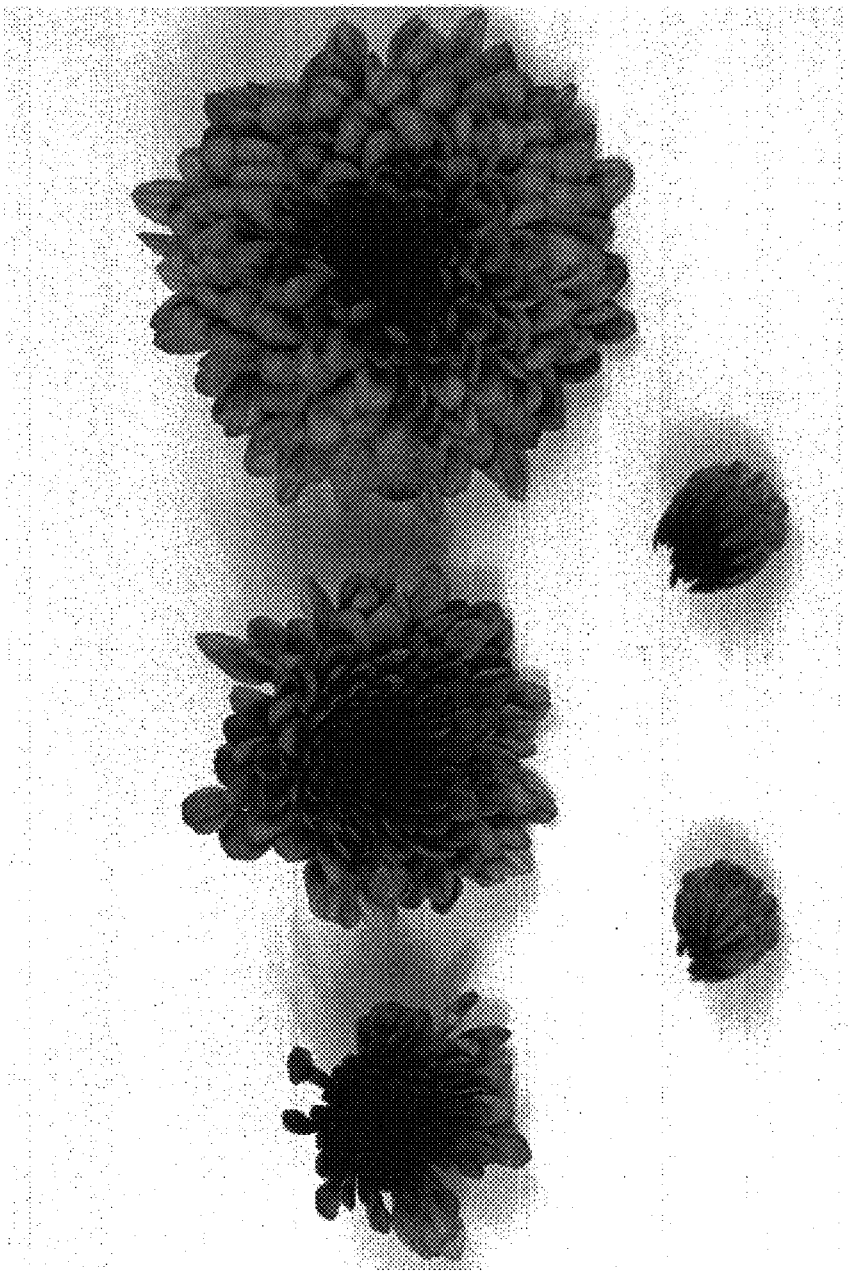
FIG. 2 shows the various stages of bloom of the new cultivar.
Figure 3:
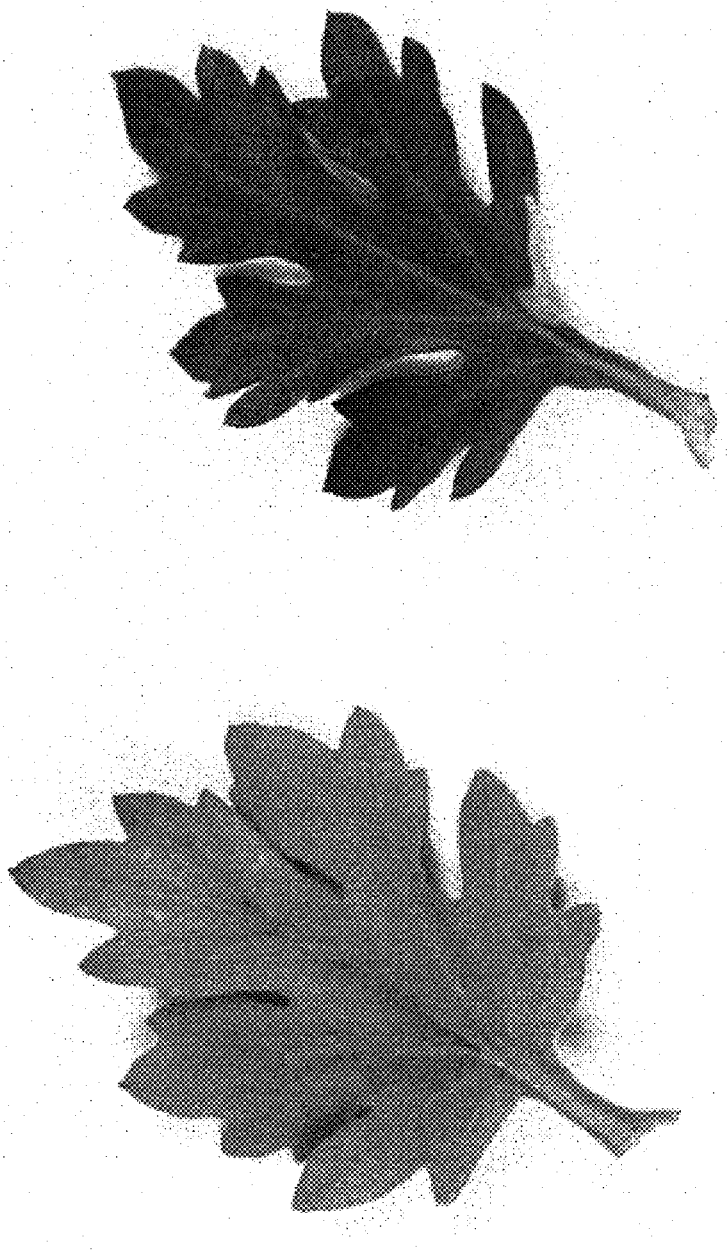
FIG. 3 shows the petiole and foliage of the new cultivar.

This new variety of chrysanthemum is of the botanical classification *Chrysanthemum morifolium.* The observations and measurements were gathered from plants grown out door in Rijsenhout, Holland under natural day length and temperature and planted week 22 in 2000 and 2001. The natural blooming date of this crop was September 4–9 (week 36). The average height of the plants was 32–38 cms. No growth retardants were used. No tests were done on disease or insects resistance or susceptibility. No tests were done on cold or drought resistance. This new variety produces medium sized blooms with white ray florets and a white center blooming for a period of 7 weeks.

When 'Amor' and 'Amor Dark Pink' are being compared the following differences and similarities are noticed: The differences of 'Amor' and 'Amor Dark Pink' are (1) the flower color (2) flower size and ray-floret form. All other characteristics of 'Amor' and 'Amor Dark Pink' are similar.

(1) 'Amor Dark Pink' is a color mutant of Amor, bearing dark pink blooms instead of pink blooms.

(2) Flower size and form. The flowers of 'Amor Dark Pink' are smaller and the ray-florets are more tubular with a spatulate tip.

The following is a description of the plant and characteristics that distinguish 'Amor Dark Pink' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Table 1: Botanical Description of Cultivar 'Amor Dark Pink'

Bud:
- *Size.*—Medium; cross-section 1.2 cm, height 1.0 cm.
- *Outside color.*—Red 54 C.
- *Involucral bracts.*—2 rows, length 7 mm, width 3 mm.
- *Involucral bracts among disc-florets.*—Not present.
- *Involucral bracts color.*—Green 138 B.

Bloom:
- *Type.*—Decorative.
- *Height.*—High, 3.0–3.5 cm.
- *Size.*—Medium.
- *Fully expanded.*—4.7–5.3 cm.
- *Number of blooms per branch.*—Approx. 5 blooms per branch.
- *Performance on the plant.*—7 weeks.
- *Seeds (if crossed).*—Produced in small quantities, ovate Grey-brown 199 A, 1½ mm in length.
- *Fragrance.*—Typical chrysanthemum, slight.

Color:
- *Center of the flower.*—Immature Red-Purple 63 A. Mature Red-purple 63 A.

*Color of upper surface of the ray-florets.*—Red-purple 63 C.

*Color of the lower surface of the ray-florets.*—Red-purple 65 A.

*Tonality from distance.*—A mounded decorative garden mum with dark pink blooms.

*Color of the upper surface of the flowers after aging of the plant.*—To Red-Purple 65B.

Ray florets:

*Texture.*—Upper and under side smooth.

*Number.*—180–210.

*Cross-section.*—Concave.

*Longitudinal axis of majority.*—Incurved to straight.

*Length of corolla tube.*—Long, 1.1–1.4 cm.

*Ray-floret margin.*—Entire.

*Ray-floret length.*—2.5 cm.

*Ray-floret width.*—0.4–0.6 cm.

*Ratio length / width.*—High.

*Shape of tip.*—Spatulate.

*Disc florets.*—Not present.

Reproductive organs:

*Stamen.*—Not present.

*Pollen.*—Not present

*Styles.*—Thin.

*Style color.*—Yellow-green 144 A.

*Style length.*—4 mm.

*Stigmas color.*—Yellow-green 144 A.

*Stigma width.*—1 mm.

*Ovaries.*—Enclosed in calyx.

Plant:

*Shape.*—Grown as a spray-type pot-mum, outdoor mounded and round.

*Growth habit.*—Spreading.

*Growth rate.*—Moderate.

*Height.*—32–36 cm.

*Width.*—35–40 cm.

*Stem color.*—Green 138 B.

*Stem strength.*—Strong.

*Stem brittleness.*—Present.

*Stem anthocyanin coloration.*—Present, a thin layer of greyed-red 181 A mainly at the base of the stem.

*Length of lateral branch.*—From top to bottom 12–13 cm.

*Lateral branch color.*—Green 138 B.

*Lateral branch, attachment.*—Weak.

*Branching* (*average number of lateral branches*).—Mounding and prolific with 9 breaks after pinching.

*Peduncle length.*—4.0–4.5 cm.

*Peduncle color.*—Green 138 B.

*Natural season blooming date.*—*September* 4–9.

Foliage:

*Color of mature leaves.*—Upper side green 138 A. Under side green 138 B.

*Color of immature leaves.*—Upper side green 138 A. Under side green 138 B.

*Size.*—Small; length 6 cm, width 5 cm.

*Quantity* (*number per lateral branch*).—12–14.

*Shape.*—Oval.

*Texture upper side.*—Glabrous.

*Texture under side.*—Pubescent.

*Venation arrangement.*—Palmate.

*Shape of the margin.*—Serrated.

*Shape of base of sinus between lateral lobes.*—Acute.

*Margin of sinus between lateral lobes.*—Diverging.

*Shape of base.*—Asymmetric.

*Apex.*—Mucronate.

TABLE 2

Differences with the comparison varieties (when grown under the same conditions)

| | 'AMOR DARK PINK' | 'AMOR' |
|---|---|---|
| Color of the center of the flower | Red-Purple 63 A | Red-Purple 74 B |
| Color of the upper side op the ray-florets | Red-Purple 63 C | Red-purple 74 C |
| Flower size | 4.7–5.3 cm | 5.0–5.5 cm |
| Ray-floret corolla tube | Long, 1–1.4 cm | Medium, 0.9–1.1 cm |
| Ray-floret shape of tip | Spatulate | Pointed |

I claim:

1. A new and distinct variety of chrysanthemum plant as described and illustrated.

* * * * *